US012797072B2

(12) United States Patent
Daller et al.

(10) Patent No.: US 12,797,072 B2
(45) Date of Patent: Nov. 17, 2026

(54) FUNCTIONALIZED POLYETHYLENE GLYCOL STAPLE LINE REINFORCEMENT

(71) Applicants: BAXTER INTERNATIONAL INC., Deerfield, IL (US); BAXTER HEALTHCARE SA, Glattpark (CH)

(72) Inventors: Justin Robert Daller, Cary, IL (US); Kevin Michael Lewis, Burlington, WI (US); Tim Fulghum, Lakemoor, IL (US); John Foley, Libertyville, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 620 days.

(21) Appl. No.: 17/677,570

(22) Filed: Feb. 22, 2022

(65) Prior Publication Data

US 2022/0265273 A1 Aug. 25, 2022

Related U.S. Application Data

(60) Provisional application No. 63/153,681, filed on Feb. 25, 2021.

(51) Int. Cl.

| | |
|---|---|
| ***A61F 2/00*** | (2006.01) |
| ***A61B 17/072*** | (2006.01) |
| ***A61L 24/00*** | (2006.01) |
| ***A61L 24/04*** | (2006.01) |
| ***A61L 24/10*** | (2006.01) |
| *A61B 17/00* | (2006.01) |

(52) U.S. Cl.

CPC .... *A61B 17/07292* (2013.01); *A61L 24/0042* (2013.01); *A61L 24/046* (2013.01); *A61L 24/102* (2013.01); *A61B 2017/00889* (2013.01); *A61L 2400/04* (2013.01)

(58) Field of Classification Search

CPC .... A61B 17/07292; A61B 2017/00889; A61B 2017/00004; A61B 2017/00526; A61B 2017/00893; A61B 2017/00898; A61B 2017/00951; A61L 24/0042; A61L 24/046; A61L 24/102; A61L 2400/04; A61L 24/001; A61L 24/0031

See application file for complete search history.

(56) References Cited

U.S. PATENT DOCUMENTS

| | | | | |
|---|---|---|---|---|
| 10,441,674 B2 * | 10/2019 | Hedrich | ......... | C12Y 304/21005 |
| 11,478,566 B2 * | 10/2022 | Hedrich | ................ | A61L 15/425 |
| 2011/0251574 A1 * | 10/2011 | Hedrich | .................. | A61P 17/02<br>604/368 |

FOREIGN PATENT DOCUMENTS

| | | | |
|---|---|---|---|
| EP | 2168610 | A2 | 3/2010 |
| EP | 3061471 | A1 | 8/2016 |
| WO | 2013/049799 | A1 | 4/2013 |
| WO | 2022/182646 | A1 | 9/2022 |

OTHER PUBLICATIONS

Pisapia et al. (Expert Review of Medical Devices 2019, vol. 16, No. 3, 253-256).*
Rocha et al. (Biomater. 23 (2002) 449-456).*
Limpert et al. (Am. J. Surg. (2009) 198, e60-e65).*
International Search Report and Written Opinion, mailed May 24, 2022, for International Patent Application Serial No. PCT/US2022/017291 filed on Feb. 22, 2022.

* cited by examiner

*Primary Examiner* — Michael G. Hartley
*Assistant Examiner* — Melissa J Perreira
(74) *Attorney, Agent, or Firm* — K&L Gates LLP

(57) ABSTRACT

Disclosed herein are surgical staple line reinforcement materials and methods of production and use thereof.

4 Claims, 1 Drawing Sheet

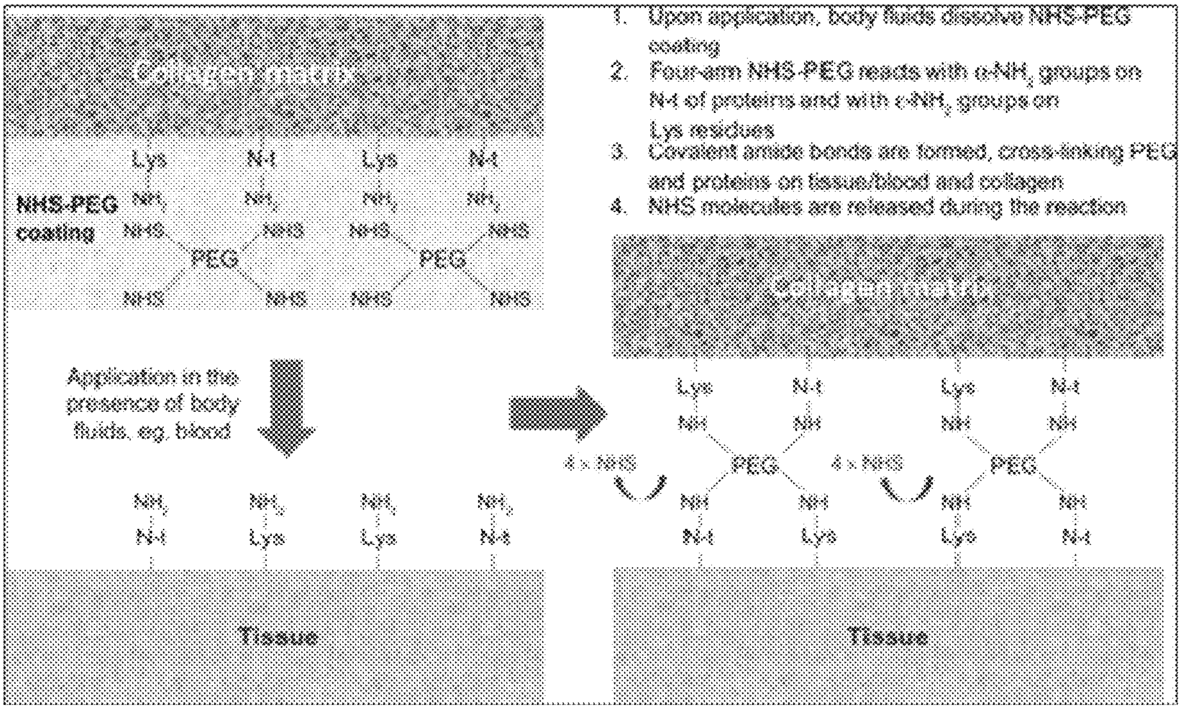

Collagen matrix
Lys
N-t
NH2
NHS-PEG coating
NHS
PEG
Application in the presence of body fluids, eg. blood
Tissue
1. Upon application, body fluids dissolve NHS-PEG coating
2. Four-arm NHS-PEG reacts with α-NH2 groups on N-t of proteins and with ε-NH2 groups on Lys residues
3. Covalent amide bonds are formed, cross-linking PEG and proteins on tissue/blood and collagen
4. NHS molecules are released during the reaction
NH
4 × NHS

FUNCTIONALIZED POLYETHYLENE GLYCOL STAPLE LINE REINFORCEMENT

CROSS-REFERENCE TO RELATED APPLICATIONS

This application claims the benefit of priority to U.S. Application No. 63/153,681, filed Feb. 25, 2021, which is herein incorporated by reference in its entirety.

FIELD

The present disclosure relates to the production and employment of materials for use in preventing operative bleeding.

BACKGROUND

Closure of surgical incisions is critical to achieving positive patient outcomes. Surgical staples are specialized staples used in place of sutures to close skin wounds. The use of staples over sutures reduces the local inflammatory response, width of the wound, and the time required for wound closure.

Current systems can also employ further materials to aid in incision closure and wound healing. For example, PERI-STRIPS DRY® with VERITAS® Collagen Matrix (PSDV) Reinforcement is intended for use as a prosthesis for the surgical repair of soft tissue deficiencies using surgical staplers when staple line reinforcement is needed. The collagen matrix is a biologic xenograft derived from bovine pericardium and created from proprietary tissue processing that provides high levels of biocompatibility (based on histological features), while maintaining the intrinsic suppleness and strength of the material. As an a-cellular non-crosslinked collagen matrix, VERITAS® Collagen Matrix was developed to promote seamless integration into the surrounding tissue through remodeling.

While current methods and devices are effective, improvements are needed with regard to adherence, hemostatic, and sealing properties that current commercially-available products lack. For example, the number of bariatric operations performed worldwide is continuously rising. Based on the an International Federation for the Surgery of Obesity and Metabolic Disorders (IFSO) survey in 2014, a total of 579,517 procedures involving sleeve gastrectomy (SG) or the Roux-en-Y gastric bypass (RYGB), which represent the two most popular techniques (45.9 and 39.6%, respectively), have been performed. Each operation predisposes to specific postoperative complications because of the presence of multiple sequential or crossing staple lines and anastomoses (gastro-entero; entero-entero). The most frequent postoperative complications after bariatric surgery are bleeding, leaks, and stenosis of the anastomosis.

Therefore, improved systems, devices, and methods are desirable.

SUMMARY

The instant disclosure provides a novel class of surgical staple line reinforcement systems, devices, and methods. Disclosed embodiments provide increased adherence, hemostatic, and sealing properties as compared to current technology. In embodiments, a biocompatible matrix or substrate material, for example a collagen matrix material such as non-crosslinked bovine pericardium, is modified prior to use, for example by the addition of a self-expanding polymer such as NHS-PEG (N-hydroxylsuccinimide functionalized polyethylene glycol) coating, to provide increased adherence, hemostatic, and sealing properties that current commercially-available products lack. This NHS-PEG enhancement is an improvement over known glue-applied buttress materials.

Disclosed embodiments comprise covalent bonding among the biocompatible matrix, the self-expanding polymer, and tissue surface, resulting from adding a surface coating of, for example, NHS-PEG on to a collagen matrix, and hemostatic properties are achieved by an increased compression along the staple line and collagen matrix buttress resulting from the swelling of the self-expanding polymer. During use, the NHS-PEG forms a hydrogel layer that bonds with the biocompatible matrix, the tissue, and also self-crosslinks, increasing adherence to a treatment area to prevent slippage or misplacement.

Sealing properties are improved by the increased adherence and compression resulting from the combination of self-expanding polymer and the collagen matrix along the staple line. The combination of these properties advances the utility of staple line buttresses when used on tissue, specifically friable or diseased tissue (e.g., emphysematous lung parenchyma, cirrhotic liver parenchyma, inflamed or denuded bowel, etc.). As no existing staple line reinforcement technology has the disclosed attributes, this is a significant and novel improvement for the repair of soft tissue deficiencies using surgical staplers when staple line reinforcement is needed.

Disclosed embodiments comprise a biocompatible matrix, for example a collagen matrix coated with a self-expanding polymer, for example NHS-PEG.

Disclosed embodiments comprise a self-expanding polymer, for example NHS-PEG, covalently bonded to a biocompatible matrix, for example a collagen matrix.

Disclosed embodiments comprise a staple line reinforcement material comprising a biocompatible matrix, for example a collagen matrix, and a self-expanding polymer, for example NHS-PEG.

Disclosed embodiments comprise methods of producing a biocompatible matrix, for example a collagen matrix, coated with a self-expanding polymer, for example NHS-PEG.

Disclosed embodiments comprise methods of use for the surgical repair of soft tissue deficiencies using surgical staplers when staple line reinforcement is advantageous.

Embodiments can comprise use with linear or circular staple lines, or combinations thereof. Disclosed embodiments comprise methods of use for the surgical repair of soft tissue deficiencies such as abdominal and thoracic wall repair, muscle flap reinforcement and repair of hernias. Disclosed embodiments can improve surgical outcomes such as blood loss, need for transfusion(s), complications, and surgical revision, reducing hospital stay duration.

In embodiments, upon application, body fluids dissolve the NHS-PEG coating. Then, four-arm NHS-PEG reacts with $NH_2$ groups of tissue proteins. Covalent amide bonds are formed, cross-linking the PEG and the tissue proteins. During the reaction, NHS molecules are released (see FIG. 1).

BRIEF DESCRIPTION OF THE DRAWING

FIG. 1 shows a schematic demonstrating the mechanism of action of a disclosed embodiment.

DETAILED DESCRIPTION

Disclosed embodiments provide improved staple line reinforcement technologies with increased adherence and compression along the staple line.

Definitions

"Administration," or "to administer" means the step of giving (i.e. administering) a hemostatic system, device, material agent, or combination thereof to a subject. The materials disclosed herein can be administered via a number of appropriate routes.

"Hemostatic agent" means an agent that can initiate and stabilize blood clot growth during bleeding, including biologics such as fibrin, thrombin, small molecules such as tranexamic acid (TXA), peptides such as Thrombin Receptor Activating Peptides (TRAPs), inorganic materials such as kaolin, and mechanical means such as expanding foams.

"Patient" means a human or non-human subject receiving medical or veterinary care.

"Therapeutically effective amount" means the level, amount or concentration of an agent, material, or composition needed to achieve a treatment goal.

"Treat," "treating," or "treatment" means an alleviation or a reduction (which includes some reduction, a significant reduction, a near total reduction, and a total reduction), resolution or prevention (temporarily or permanently) of a symptom, disease, disorder or condition, so as to achieve a desired therapeutic result, such as by reducing blood loss or healing of injured or damaged tissue.

Biocompatible Substrates/Matrices

Disclosed embodiments comprise biocompatible matrices or substrates comprising a presenting nucleophilic group (e.g. amine, thiol etc.). Additional embodiments comprise substrates that are porous, for example a substrate that has sufficient surface imperfections to allow self-expanding polymer attachment can be utilized and act as a supporting reinforcement layer.

In embodiments, the biocompatible matrix can be any matrix that is usable for being administered to human patients, especially for wound coverage or filling of volumetric defects (e.g. in organs) of a human patient, and that does not induce a negative effect in the course of this administration. A biocompatible matrix is one that does not contain materials or components that threaten, poison, impede, or adversely affect living tissue (e.g. human tissue that is exposed to the surface in wounds). Examples of such matrices are "classical" wound coverages, such as knitwear, patches and sponges, and the like.

In embodiments, the biocompatible matrix is a hemostatic matrix, i.e. the matrix material as such has already hemostatic properties. Such materials are available in the art and comprise, for example, collagen, gelatin or chitosan. Further suitable matrices can comprise a biomaterial, preferably a protein, a biopolymer or a polysaccharide matrix, especially a collagen, gelatin, fibrin, starch or chitosan matrix; or a synthetic polymer, for example a polyvinyl alcohol (PVA), polyethylene glycol, poly(N-isopropylacrylamide), etc.

In embodiments, the biocompatible matrix is biodegradable, i.e. it is naturally absorbed by the patient's body after some time. In embodiments, the material (including the matrix) is biocompatible, i.e. have no harming effect to the patient to whom the material is administered. Such biodegradable materials are specifically suitable in situations where hemostasis is achieved inside the body, i.e. in the course of surgery when the site is closed after the procedure.

Thus, the biocompatible matrix can be a biomaterial selected from biopolymers such as a proteins or polysaccharides, for example a biomaterial such as collagen, gelatin, fibrin, a polysaccharide, e.g. hyaluronic acids, chitosan, and derivatives thereof, collagen, chitosan, etc.

Disclosed biocompatible matrices can be obtained from any suitable source including mammalian sources, e.g., in the form of collagenous connective tissue with three dimensional intertwined fibers. Such tissues generally include serous and fibroserous membranes. In a particularly preferred embodiment, the tissue source is selected from bovine pericardium, peritoneum, fascia lata, dura mater, dermis, and small intestinal submucosa. In a further preferred embodiment, the tissue is bovine pericardium, and is treated to provide the treated tissue with an optimal combination of biocompatibility, thickness, and other physical and physiological properties.

In embodiments, disclosed matrices can comprise a non-crosslinked, decellularized and purified mammalian tissue (e.g., bovine pericardium) having particular use as an implantable material in a manner that is both resorbable and remodelable.

In various embodiments, the matrix comprises a recombinant polymer. In particular, the recombinant polymer can be a recombinant human collagen, such as, for example, recombinant human collagen type I, recombinant human collagen type III, or a combination thereof. In one embodiment, the matrix comprises recombinant human collagen type III. In another embodiment, the matrix comprises recombinant human collagen type I. For example, the recombinant human gelatin can be derived from recombinant human collagen type III. In yet another embodiment, the matrix comprises recombinant gelatin derived from recombinant human collagen type I. In further embodiments, the matrix comprises recombinant gelatin produced directly by expression of encoding polynucleotide.

In embodiments, a disclosed collagen matrix is treated by a process that includes alkylating a major percentage of its available amine groups to an extent sufficient to permit the tissue to be implanted and used in vivo. Preferably a tissue is processed by alkylating its amines to an extent sufficient to react 80% or more, preferably 90% or more, and most preferably 95% or more of the amine groups originally present. The efficacy and extent of alkylation can be determined by a variety of means.

Matrices and substrates described herein can have any suitable form that is usable for the treatment of patients in need of a hemostatic material, i.e. as a planar form (where the third dimension extension is comparably small (e.g. less than 1/10 or 1/20) compared to the other two dimensions; or as a three-dimensional form (e.g. a sponge, a paste, a cavity implant, etc.). Planar or three-dimensional embodiments of the hemostatic material described herein can, for example, be sponges, woven or non-woven fabrics, preformed shapes, such as a cylinders or cones (e.g. for tooth extraction) or as flexible or non-flexible scaffolds, or sheets. Furthermore, the material can be flexible and suitable to be applied on diverse tissues and locations with various shapes.

Self-Expanding Polymer

Disclosed embodiments comprise a biocompatible matrix, for example one coated with, for example, a self-expanding polymer such as PEG. Embodiments comprise a biocompatible matrix coated with pentaerythritol polyethylene glycol ether tetra-succinimidyl glutarate (NHS-PEG), an amino (—$NH_2$) reactive PEG derivative that can be used to modify protein, peptide or any other surfaces with their available amino groups. NHS esters react with primary amine groups at pH 7~8.5 to form stable amide bonds.

Disclosed matrices and substrates can further comprise an activator or proactivator of blood coagulation, including fibrinogen, thrombin or a thrombin precursor. Thrombin or the precursor of thrombin is understood as a protein that has thrombin activity and that induces thrombin activity when it is contacted with blood or after application to the patient, respectively. Its activity is expressed as thrombin activity (NIH-Unit) or thrombin equivalent activity developing the corresponding NIH-Unit. The activity in disclosed embodiments can be 100-10,000, preferably 500-5,000. A protein with thrombin activity can comprise, for example, alpha-thrombin, meizothrombin, a thrombin derivative or a recombinant thrombin. A suitable precursor can comprise, for example, prothrombin, factor Xa optionally together with phospholipids, factor IXa, activated prothrombin complex, FEIBA, any activator or a proactivator of the intrinsic or extrinsic coagulation, or mixtures thereof.

Disclosed embodiments can be used together with further physiologic substances. For example, in embodiments the matrix further comprises pharmacologically active substances, among them antifibrinolytics, such as a plasminogenactivator-inhibitor or a plasmin inhibitor or an inactivator of fibrinolytics.

As a further pharmacologically active substance an antibiotic, such as an antibacterial or antimycotic can be used together with the matrix, for example as a component homogeneously distributed in the sponge. Further bioactive substances such as growth factors and/or pain killers may be also present.

Further combinations are disclosed with specific enzymes or enzyme inhibitors, which can regulate, i.e. accelerate or inhibit, the resorption of the sponge. Among those are collagenase, its enhancers or inhibitors. Also, a suitable preservative can be used with disclosed matrices.

Commercial Products/Kits

The present staple line reinforcement material can be finished as a commercial product by the usual steps performed in the present field, for example by appropriate sterilization and packaging steps. For example, the present material may be treated by UV/vis irradiation (200-500 nm), for example using photo-initiators with different absorption wavelengths (e.g. Irgacure 184, 2959), preferably water-soluble initiators (Irgacure 2959). Such irradiation is usually performed for an irradiation time of 1-60 min, but longer irradiation times may be applied, depending on the specific method. The material according to the present disclosure can be finally sterile-wrapped so as to retain sterility until use and packaged (e.g. by the addition of specific product information leaflets) into suitable containers (boxes, etc.).

Disclosed embodiments can also be provided in kit form combined with other components necessary for administration of the material to the patient. The kit may further contain means for administering or preparing for administering the hemostatic material, such as syringes, tubes, catheters, forceps, scissors, sterilizing pads or lotions, etc.

Disclosed kits, such as for use in surgery and/or in the treatment of injuries and/or wounds, can comprise a disclosed hemostatic material and at least one administration device, for example a buffer, a syringe, a tube, a catheter, forceps, scissors, gauze, a sterilizing pad or lotion.

In embodiments, the buffer solution further comprises an anti-bacterial agent, immunosuppressive agent, anti-inflammatory agent, anti-fibrinolytic agent, especially aprotinin or ECEA, growth factor, vitamin, cell, or mixtures thereof. Alternatively, the kit can also further comprise an anti-bacterial agent, immunosuppressive agent, anti-inflammatory agent, anti-fibrinolytic agent, especially aprotinin or ECEA, growth factor, vitamin, cell, or mixtures thereof.

The kits are designed in various forms based on the specific deficiencies they are designed to treat.

Methods of Manufacture

Disclosed substrates and matrices can be coated, or impregnated, or both with a self-expanding polymer such as PEG, for example NHS-PEG, for example wherein the matrix and the self-expanding polymer are associated with each other so that the reactivity of the self-expanding polymer is retained, and the self-expanding polymer is coated onto a surface of the matrix, or the matrix is impregnated with the self-expanding polymer, or both. Suitable self-expanding polymers can comprise a polyalkylene oxide polymer such as polyethylene glycol (PEG), for example NHS-PEG.

In embodiments, the molecular weight of the self-expanding polymer component can be in a range of 500 to 50,000, most preferred about 10,000.

Disclosed embodiments can comprise a combination of impregnated and coated forms. The amount of coating of self-expanding polymer component on the matrix can be from about 1 mg/cm$^2$ to about 20 mg/cm$^2$, more preferred about 2 mg/cm$^2$ to about 14 mg/cm$^2$. The concentration of self-expanding polymer can be, for example, about 5 mg/cm$^3$ to about 100 mg/cm$^3$, or about 100 mg/cm$^3$ to about 70 mg/cm$^3$ for an impregnated matrix.

Further methods of manufacture can comprise, for example, providing a matrix of a biomaterial in dried form, providing at least one reactive self-expanding polymeric material in the form of dry powder, contacting the biomaterial and the self-expanding polymeric material so that the self-expanding polymeric material is present on at least one surface of the matrix, and fixing the self-expanding polymeric material on the sponge. In some cases, the process of fixing can be achieved by melting at temperatures between 30° C. to 80° C., preferably between 60° C. to 65° C., for a time period sufficient for fixing, preferably between 1 minute to 10 minutes, especially about 4 minutes. In yet another aspect, embodiments comprise methods for manufacturing a hemostatic staple line reinforcement material which can include providing a matrix of a biomaterial in dried form, providing a reactive self-expanding polymeric material in the form of a solution, contacting the biomaterial and the self-expanding polymeric material so that the biomaterial is impregnated with the self-expanding polymeric material, and drying the impregnated biomaterial.

Further embodiments relate to methods of manufacturing a staple line reinforcement material comprising:

a. providing a matrix of a biomaterial in dried form,
b. providing one self-expanding polymer material in the form of dry powder,
c. contacting a. and b. so that the material of b. is present on at least one surface of said biomaterial, and
d. fixing the material of b. on the matrix of a.

Fixing can be achieved by melting the polymeric component onto the sponge in a pre-heated oven, e.g. at temperatures between 30° C. to 80° C., preferably between 60° C. to 65° C., for a time period sufficient for fixing, e.g. between 1 minute to 10 minutes, preferably about 4 minutes. Alternatively fixing can be achieved by an infrared heater or any other heat source. The distance between the pad and the heater, the intensity of the heater and the time of exposure to infrared irradiation are adjusted to achieve melting of the coating at a minimum of heat exposure.

Further embodiments relate to methods of manufacturing a staple line reinforcement material comprising:

a. providing a matrix comprising a matrix of a biomaterial in dried form, b. providing one reactive self-expanding polymer material in the form of a solution, e.g. an aqueous solution with a pH of lower than 5, preferably about 3 or a water free organic solvent based solution, e.g. based on ethanol, acetone, methylenechloride and the like, c. contacting a. and b. so that the material of a. is impregnated with b., and drying the material obtained in step c).

Contacting for achieving impregnation can be done by placing the self-expanding polymer solution on top of the sponge and letting the solution soak into said matrix for a time period sufficient for absorption, e.g. from about 2 minutes to about 2 hours, preferably 30 minutes.

Drying can include freeze drying or air drying and comprises removing volatile fluid components.

Methods of Use

Methods of use of disclosed embodiments can comprise application to a site where bleeding is desired to be reduced, such as a site of injury or surgical procedure. For example, disclosed embodiments comprise methods of use for the surgical repair of soft tissue deficiencies using surgical staplers when staple line reinforcement is needed. Embodiments can comprise use with linear or circular staple lines, or combinations thereof. For example, disclosed embodiments comprise methods of use as reinforcement of staple lines during gastric, bariatric, and small bowel, mesentery, colon, and colorectal procedures.

Disclosed embodiments comprise methods of use as an implant for the surgical repair of soft tissue deficiencies such as abdominal and thoracic wall repair, muscle flap reinforcement and repair of hernias (e.g., diaphragmatic, femoral, incisional, inguinal, lumbar, paracolostomy, scrotal, umbilical), reconstruction of the pelvic floor excluding transvaginal pelvic organ prolapse, repair of rectal prolapse excluding rectocele, and for use as an implant for the surgical repair of soft tissue deficiencies.

Disclosed embodiments can be used in connection with cardiac, neurological, urological, and endocrine-related surgical procedures.

Disclosed embodiments can be provided in any suitable form, e.g., as flat or textured sheets or strips.

These methods are further described in the following Examples.

EXAMPLES

The following non-limiting Examples are provided for illustrative purposes only in order to facilitate a more complete understanding of representative embodiments. This example should not be construed to limit any of the embodiments described in the present specification.

Example 1

Use of the Staple Line Reinforcement

Check the heat indicator on the carton. Do not use the product if the heat indicator is activated.

Remove the pouch from the carton.

Inspect the outer pouch. Do not use if the outer pouch is damaged or if the seals are not intact.

Open the outer pouch and aseptically transfer the inner pouch into the sterile field.

Open the inner pouch and remove the NHS-PEG coated collagen substrate with a smooth forceps.

The coated biocompatible substrate is ready for use. If the device is not to be used immediately, keep it moist by placing it in a basin of room temperature sterile saline. Caution: device must be moist at all times; place the device in a solution of room temperature saline for up to one hour if needed.

At the surgeon's discretion a room temperature, pre-implant soak in saline and antibiotics for up to one hour may be conducted.

a. Implant instructions:

i. Using sterile technique, tailor the configurations of the device to meet the patient's needs.

ii. The device should be placed in maximum possible contact with healthy, well-vascularized tissue; adequate overlap is recommended to ensure that the implant margin is in contact with healthy, vascularized adjacent tissue.

iii. The device be secured in position to the host tissue by suture, staple, tack, or other method chosen by the surgeon; when suturing, place the sutures at least 2-3 mm from the edge of the device.

iv. Discard any unused portion of the device.

Example 2

Use in Surgery

An 18-year-old man is diagnosed with chest wall Ewing's sarcoma. The original lesion measures 9×7.5×6.5 cm, and is described as infiltrating the chest wall at the right costovertebral angle of D8, the posterior eighth rib, and the overlying adjacent paraspinal muscles. Four cycles of neoadjuvant chemotherapy (etoposide plus ifosfamide alternating to vincristine or adriamycin and cyclophosphamide) are administered yielding a significant reduction of the visible mass (down to 5 cm in greater diameter). At surgery, an en bloc resection of the posterior segments of ribs 7 to 9, along with partial vertebrectomy of the corresponding bodies is performed, and the spine is stabilized.

Although intraspinal ligation of the intercostal nerve roots is completed, a minimal tear of the dura is recognized and sealed with tissue glue. Given the site and geometrical characteristics of the defect, a 25×12 cm patch of acellular NHS-PEG coated collagen matrix is used as the sole reconstructive material. The patch is stretched and anchored to the stabilizer and to the surrounding ribs. Previously raised latissimus dorsi and trapezius muscle flaps are used to cover the patch, thus ensuring acceptable chest wall rigidity and tightness. The postoperative course is uneventful. Two months after the surgery, a chest computed tomographic scan shows satisfactory postsurgical results. At 8 months after diagnosis, and after a 3-month follow-up from the operation, the patient is well and disease-free.

Example 3

Use in Surgery

A patient undergoes surgery associated with the bowel. Following the surgery, a disclosed collagen substrate comprising an NHS-PEG coating is applied to the incision area, then surgical staples are used to close the surgical incision.

Example 4

Use in Surgery

A patient undergoes surgery associated with the lungs. Following the surgery, a disclosed substrate comprising an NHS-PEG coating is applied to the incision area, then surgical staples are used to close the surgical incision.

Example 5

Use in Surgery

A patient undergoes surgery associated with the liver. Following the surgery, a disclosed substrate comprising an NHS-PEG coating is applied to the incision area, then surgical staples are used to close the surgical incision.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, comprising the best mode known to the inventor for carrying out the methods and devices described herein. Of course, variations on these described embodiments will become apparent to those of ordinary skill in the art upon reading the foregoing description. Accordingly, this disclosure comprises all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be comprised in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

The invention claimed is:

1. A method of manufacturing a device for compressing a surgical staple line, said device comprising a collagen matrix, the collagen matrix comprising non-crosslinked bovine pericardium, and the device further comprising a self-expanding polymer comprising NHS-PEG; said method comprising:

providing the collagen matrix in dried form;

providing the NHS-PEG in a water free organic solvent solution based on ethanol, acetone, or methylenechloride;

contacting the collagen matrix with the NHS-PEG;

drying the collagen matrix; and treating the collagen matrix by a process including alkylating amine groups of the collagen matrix.

2. The method of claim 1, wherein said water free organic solvent solution is based on ethanol.

3. The method of claim 1, wherein said water free organic solvent solution is based on acetone.

4. The method of claim 1, wherein said water free organic solvent solution is based on methylenechloride.

* * * * *